United States Patent [19]
Richter et al.

[11] Patent Number: 6,107,484
[45] Date of Patent: Aug. 22, 2000

[54] PROCESS FOR PREPARING POLYISOCYANATES CONTAINING IMINOOXADIAZINEDIONE GROUPS

[75] Inventors: Frank Richter; Stefan Groth, both of Leverkusen; Eberhard Stelter; Wilfried Litz, both of Köln, all of Germany

[73] Assignee: Bayer Aktiengesellschaft, Leverkusen, Germany

[21] Appl. No.: 09/320,366

[22] Filed: May 25, 1999

[30] Foreign Application Priority Data

Jun. 2, 1998 [DE] Germany .............................. 198 24 490
Jun. 2, 1998 [DE] Germany .............................. 198 24 485

[51] Int. Cl.$^7$ ...................... C07D 273/04; C07D 251/34; C08G 18/79
[52] U.S. Cl. ................................ 544/67; 528/51; 528/52; 528/73; 544/193; 544/222
[58] Field of Search .................................. 528/51, 52, 73; 544/67, 193, 222

[56] References Cited

U.S. PATENT DOCUMENTS

| | | | |
|---|---|---|---|
| 4,736,008 | 4/1988 | Kouno et al. | 528/57 |
| 4,785,069 | 11/1988 | Kouno et al. | 528/51 |
| 4,937,339 | 6/1990 | Shiomura et al. | 544/193 |
| 4,960,848 | 10/1990 | Scholl et al. | 528/48 |
| 4,992,548 | 2/1991 | Scholl et al. | 544/193 |
| 5,013,838 | 5/1991 | Scholl | 544/193 |
| 5,717,091 | 2/1998 | Richter et al. | 544/67 |
| 5,882,544 | 3/1999 | Richter et al. | 544/67 |
| 5,914,383 | 6/1999 | Richter et al. | 528/59 |
| 6,020,066 | 2/2000 | Weisser et al. | 528/73 |

FOREIGN PATENT DOCUMENTS

| | | |
|---|---|---|
| 2200823 | 9/1997 | Canada . |
| 2244486 | 2/1999 | Canada . |
| 447 074 | 9/1991 | European Pat. Off. . |
| 841 088 | 5/1998 | European Pat. Off. . |

OTHER PUBLICATIONS

Nambu Y et al: "Synthesis of novel aromatic isocyanurates by the fluoride–catalyzed selective trimerization of isocyanates" Journal of Organic Chemistry, Bd. 58, Nr. 7, 1993, Seiten 1932–4, XP002113530.

J. Thermal Anal. (month unavailable) 1983, pp. 215–228.

*Primary Examiner*—Rabon Sergent
*Attorney, Agent, or Firm*—Joseph C. Gil; Thomas W. Roy

[57] ABSTRACT

The present invention relates to a process for the production of trimerized polyisocyanates containing at least 30 mole % of iminooxadiazinedione groups (asymmetric trimers) in the trimer mixture by catalytically trimerizing a starting isocyanate selected from organic di- or polyisocyanates having a number average molecular weight of 140 to 600 and containing aliphatically, cycloaliphatically and/or araliphatically bound isocyanate groups in the presence of quaternary ammonium and phosphonium fluoride trimerization catalysts corresponding to the formula $$R_4E^+F^- \qquad (I),$$

wherein

E represents N or P and

R represents identical or different, optionally branched, aliphatic, aromatic and/or araliphatic $C_1$–$C_{20}$ groups, or two or more R groups may also form, with one another and with the nitrogen or phosphorus atom, saturated or unsaturated rings, in which the catalysts are i) present in pure form, ii) blended with solvating agents S for the fluoride anion, wherein S is selected from protic compounds having a $pK_a$ value of greater than 2 (determined in $H_2O$ at 25° C.) or oxalic acid, provided that the molar ratio of organic acid to fluoride ion, $F^-$, does not exceed 20 and provided that S is not HF or an alcohol having a functionality of 2 or more, or iii) blended with water, wherein the molar ratio of water to fluoride ions ($F^-$) does not exceed a value of 10.

4 Claims, No Drawings

PROCESS FOR PREPARING POLYISOCYANATES CONTAINING IMINOOXADIAZINEDIONE GROUPS

BACKGROUND OF THE INVENTION

1. Field of the Invention

The present invention relates to a process for the production of polyisocyanates containing iminooxadiazinedione groups.

2. Description of the Prior Art

Polyisocyanates containing iminooxadiazinedione groups (asymmetric trimers) are high grade raw materials, which may be used for the production of polyurethane lacquers and coatings (DE-A 19,611,849). These polyisocyanates are present as a subsidiary component in the well known polyisocyanates containing isocyanurate groups (symmetric trimers).

Isocyanate oligomers having a significantly increased iminooxadiazinedione content are described in DE-A 19,611,849. Their advantageous properties, for example, as a raw material for the manufacture of polyurethane lacquers and coatings, are described. For isocyanate oligomers having at least three NCO groups, poly(di)-isocyanates containing iminooxadiazinedione groups have the lowest viscosity.

DE-A 19,611,849 describes the use of hydrogen (poly) fluorides corresponding to the formula, $M[nF^- \cdot (HF)_m]$, wherein $^m/_n$ is >0 and M represents an n-charged cation or an n-valent residue, as a catalyst for isocyanate trimerization with preferential formation of iminooxadiazinedione groups. This process is disadvantageous requires it handling HF during the production of the catalysts, which usually starts from the corresponding fluorides, $M[nF^-]$, wherein M is an n-charged cation.

The handling of HF restricts the technical feasibility of the entire process because particular precautions are required for handling, optionally anhydrous, hydrofluoric acid which greatly complicates the production of the catalyst. In addition, due to the corrosiveness of the material, certain requirements arise with regard to the selection of the reactors in which the catalyst may be produced and used. These circumstances restrict the widespread, safe performance of the isocyanate trimerization process when it is desired to form a high proportion of iminooxadiazinedione groups.

An object of the present invention is to provide a process that does not require hydrofluoric acid to be handled during the production of the catalysts, but still yields products having an elevated content of iminooxadiazinedione groups in the trimer mixture. The term "trimer mixture" means the sum of isocyanurate and iminooxadiazinedione groups. An elevated iminooxadiazinedione group content means products containing at least 30% of iminooxadiazinedione groups in the trimer mixture.

This object may be achieved with the process of the present invention described hereinafter, in which isocyanate trimerization is catalyzed by quaternary ammonium or phosphonium fluorides.

SUMMARY OF THE INVENTION

The present invention relates to a process for the production of trimerized polyisocyanates containing at least 30 mole % of iminooxadiazinedione groups (asymmetric trimers) in the trimer mixture by catalytically trimerizing a starting isocyanate selected from organic di- or polyisocyanates having a number average molecular weight of 140 to 600 and containing aliphatically, cycloaliphatically and/or araliphatically bound isocyanate groups in the presence of quaternary ammonium and phosphonium fluoride trimerization catalysts corresponding to the formula $$R_4E^+F^- \qquad (I),$$

wherein

E represents N or P and

R represents identical or different, optionally branched, aliphatic, aromatic and/or araliphatic $C_1$–$C_{20}$ groups, or two or more R groups may also form, with one another and with the nitrogen or phosphorus atom, saturated or unsaturated rings, in which the catalysts are i) present in pure form, ii) blended with solvating agents S for the fluoride anion, wherein S is selected from protic compounds having a $pK_a$ value of greater than 2 (determined in $H_2O$ at 25° C.) or oxalic acid, provided that the molar ratio of organic acid to fluoride ion, $F^-$, does not exceed 20 and provided that S is not HF or an alcohol having a functionality of 2 or more, or iii) blended with water, wherein the molar ratio of water to fluoride ions ($F^-$) does not exceed a value of 10.

DETAILED DESCRIPTION OF THE INVENTION

In the process of the present invention the starting isocyanate is preferably an aliphatic diisocyanate having a molecular weight of 140 to 300 or mixtures thereof and the trimerized polyisocyanates preferably contain at least 35%, more preferably at least 40 mole % of iminooxadiazinedione groups (asymmetric trimers) in the trimer mixture.

Preferred trimerization catalysts are quaternary ammonium or phosphonium fluorides of formula (I) blended with monofunctional alcohols or alcohol mixtures having a number average molecular weight of 32 to 250, wherein the concentration of the quaternary ammonium or phosphonium fluoride in the mixture is at least 20 wt. %, more preferably at least 30 wt. %.

In the process of the present invention the molar ratio of organic acid to fluoride ions, $F^-$, preferably does not exceed 10, more preferably does not exceed 5 and most preferably does not exceed 2. Also when the catalyst is blended with water, the molar ratio of water to fluoride ions ($F^-$) preferably does not exceed 5. The nature and extent of solvation of the fluoride anions are critical to the performance of the process of the present invention.

One feature of the proposed process which is essential to the invention is to use the tetraalkylphosphonium or -ammonium fluoride catalyst in as concentrated a form as possible, preferably introducing virtually pure active substance into the trimerization. This is subject to practical limits arising from the requirements for industrial handling of the catalyst. The solubility or rapid, homogeneous distribution of solid catalysts or highly concentrated and thus relatively highly viscous catalyst solutions in the starting isocyanate is sometimes too low such that it is impossible to prevent spontaneous formation of gel particles as a result of localized crosslinking.

In this connection it is an essential characteristic of S that its complexing characteristics for the fluoride ion must be arranged such that, at least until the catalyst is homogeneously distributed in the starting isocyanate, the catalytic activity of the fluoride anion develops slowly ("slow release" mechanism). Otherwise, spontaneous crosslinking may occur which results in the formation of turbid, unusable products. While this may indeed be countered by greater dilution of the catalyst, this surprisingly results in an increasingly lower iminooxadiazinedione content in the trimer mixture (c.f. Example 4).

It is thus particularly preferred to use liquid tetraalkylammonium or -phosphonium fluorides as the trimerization catalyst. However, it is also possible to use solid compounds as the pure substance which become liquid upon the addition of even very small quantities of S, such as tetrabutylammonium or tetrabutylphosphonium fluoride.

Pure compounds or mixtures of compounds corresponding to formula (I) may be used as the trimerization catalyst. Examples of suitable catalysts include products which are commercially available, optionally in the form of their salts with counterions other than fluoride, which can readily be converted into the fluoride form, such as chlorides, bromides, iodides and (hydrogen) sulfates. See, for example, Synthesis 1988, 12, 953–955 and Example 1. Examples include tetrakis-(hydroxymethyl)phosphonium chloride and sulfate; and tetraethyl-, tetrabutyl-, tetraoctyl-, tetrakis (hexadecyl)-, tributyl(tetradecyl)-, tributyl(hexadecyl)- and trioctyl(octadecyl)-phosphonium chloride, bromide or iodide.

It is also possible to use phenyl(alkyl) derivatives, although they are less preferred due to their poorer solubility (when compared to the purely aliphatically substituted compounds) in the solvating agents or solvents, in particular the monofunctional alcohols, suitable for use in the isocyanate oligomerization.

The particular role played by the nature and quantity of the solvating agent(s) S used during catalysis in the preferred formation of iminooxadiazinedione groups was not expected. The molar ratio of S:F$^-$ is important to the performance of the process according to the invention in order to achieve an increased content of iminooxadiazinedione groups of at least 30 mole % in the trimer mixture.

The surprising observation that the selectivity of the catalysis is significantly dependent upon the concentration of the catalyst distinguishes the present invention from prior publications which also describe the use of fluorides for isocyanate trimerization with isocyanurate formation.

DE-A 3,827,596 describes the possibility of producing polyisocyanates containing isocyanurate groups using quaternary ammonium and phosphonium fluorides. On page 3, lines 30–35, it is explicitly stated that the fluoride concentration of the solution to be used for homogeneous catalysis should not exceed 0.5 mmol. of F$^-$ per g of solution. The solvents to be used include 2-ethyl-1,3-hexanediol, acetonitrile or N,N-dimethylformamide (DMF).

However, testing performed by using the method proposed in DE-A 3,827,596, demonstrates that when these fluorides dissolved in the disclosed solvents at the fluoride ion concentration set forth (0.01 to 0.1 mmol. of F$^-$ per g of solution, i.e. approx. 0.02–0.2% F$^-$ in the catalyst solution) only results in the formation of extremely turbid products which are completely unusable as high grade isocyanate components for the production of polyurethane lacquers and coating compositions. In addition, the iminooxadiazinedione content in the trimer mixture of the products produced in this manner is low and is further reduced when the catalyst solution is more highly diluted with the disclosed solvents (Example 2, Table 1).

Aprotic catalyst solvents, such as acetonitrile or DMF, are generally poorly suited for use in the claimed process because during recovery of the unreacted monomer (for example, by distillation, which generally proceeds after (partial) trimerization of the isocyanate groups of diisocyanates such as HDI), the solvents are generally removed from the process with the monomer and are subsequently recycled. Because they are not consumed during the reaction the solvents continue to accumulate as this process is repeated such that sooner or later it is necessary to separate them from the "circulated" monomer in an elaborate process. Accordingly, this process would be very disadvantageous for economic reasons.

Also, DMF may react at elevated temperature with isocyanates to form unwanted secondary products (c.f. *Angew. Makromol. Chem.*, 1992, 197, 131–139, evolution of $CO_2$ and formation of formamidine). At low temperatures DMF, in combination with basic substances (for example from impurities), may catalyze the unwanted linear polymerization of the (poly)isocyanates to form insoluble 1-nylon compounds (for example *Organic Chemistry, A Series of Monographs*, volume 13 B/2, Acad. Press, New York & London 1972, pp. 332 et seq. and literature cited therein).

Even when relatively highly dilute catalyst solutions are used, the use of aprotic catalyst solvents such as acetonitrile and DMF results in the formation of crude trimer solutions containing very coarse, gel-like solid particles, which cannot be worked up until elaborate filtration operations have been performed and even then do not yield completely non-turbid resins after working up by thin film distillation (c.f. Examples 2b and 2c). The iminooxadiazinedione content in the resulting trimer resins is also very low (Table 1).

The examples of DE-A 3,827,596 refer only once to the production of a phosphonium fluoride catalyst, which was applied onto a solid support (silica gel) (page 6, Table 1, Example 4). No mention is made in the patent of using the catalyst for modifying isocyanates.

DE-A 3,902,078 describes similar catalyst systems, in this case in combination with $CO_2$, and their use for the production of modified polyisocyanates containing isocyanurate groups. Phosphonium salts are explicitly described as being "less preferred" than ammonium species (page 3, lines 32–33, and lines 60–61, page 4, line 12). The statements made with regard to preferred catalyst concentrations for homogeneous catalysis are similar to those already made in DE-A 3,827,596. The examples do not make any reference to the production or use of phosphonium fluorides as a catalyst for preparing modified isocyanates.

DE-A 3,902,078 also discloses that the "iminooxadiazinedione content" of the resultant products remains "subordinate" (page 4, lines 51–52). Examples 6 to 9 report the formation of iminooxadiazinediones in addition to isocyanurate and oxadiazinetrione, in which the latter two are the principal products of the reaction.

The manner of reporting this information would tend to lead one to the conclusion that the presence of $CO_2$ during the trimerization reaction is required for the formation of iminooxadiazinedione and that the iminooxadiazinediones are unwanted secondary products.

In general, neither DE-A 3,827,596 nor DE-A 3,902,078 contains any reference to the particular role played by the catalyst solvent not only in simply diluting the catalyst, but also in ensuring that the reaction proceeds in a straightforward manner, i.e., to avoid the formation of turbidity or solids, and as a selectivity-controlling agent (solvating agent) for the preferred formation of iminooxadiazinedione groups during isocyanate trimerization.

The literature makes reference to the possibility of using phosphonium fluorides, optionally generated "in situ" from an alkali metal or alkaline earth metal fluoride and another quaternary phosphonium salt (chloride, bromide etc.,), for modifying isocyanates (phase-transfer catalysis, for example *Isr. J Chem.*, 1985, 26, 222–224, but the use of phosphonium fluorides is not described therein).

In EP-A 0,315,692, which describes concept of phase transfer catalysis, potassium fluoride-catalyzed processes for the preparation of compounds having isocyanurate groups are described. The simultaneous presence of onium compounds to "increase the efficiency of the reaction" is also proposed. Also, phosphonium salts are not used in the examples. The specification primarily relates to the trimerization of aromatic isocyanates (TDI, MDI). The trimerization of isocyanates containing aliphatically bound NCO groups to form isocyanurate groups is only demonstrated by the reaction of n-butyl isocyanate with potassium fluoride in two examples. In Example 1 of EP-A 0,315,692 potassium fluoride was used as the sole catalyst; in Example 5 potassium fluoride was used in the presence of a quaternary ammonium salt (benzyltrimethylammonium chloride.

The method is not practical for use on a commercial scale because of the following disadvantages:

1) the high reaction temperature (120° C.) and the comparatively long reaction times (8 hours in Example 1, 4 hours in Example 5 of EP-A 0,315,692) with a high catalyst concentration;
2) the technically disadvantageous removal of the solid potassium salt components after the reaction by filtration (Example 1 of EP-A 0,315,692) or by washing with water, which prevents the preparation of products containing free isocyanate groups (Example 5 of EP-A 0,315,692) and
3) because of the combined of a phosphonium salt and potassium fluoride, fluoride ions are "extracted" continuously from the insoluble, inorganic phase, which is described as the actual catalyst, into the organic isocyanate-containing phase.

The reaction of isocyanates with carboxylic acids/ anhydrides using fluoride catalysts disclosed in EP-A 235, 388 yields the corresponding polyamides/imides, but not products of an NCO/NCO reaction.

None of the latter documents contains any reference to the (additional) formation of iminooxadiazinedione groups in addition to the described isocyanurate groups.

Based on the teachings of the preceding prior art it would not be apparent that quaternary ammonium- or phosphonium fluorides which are completely soluble in the organic medium are especially advantageous for the highly reproducible preparation of turbidity-free isocyanate trimer resins having a high content of iminooxadiazinedione groups in the trimer mixture.

Based on the teachings of the preceding prior art it would not be apparent that quaternary ammonium or phosphonium fluorides or specific combinations of these fluorides with certain solvating agents for fluoride anions which are completely soluble in the organic medium (generally the starting isocyanate, are especially advantageous for the production of turbidity-free isocyanate trimer resins having an increased iminooxadiazine-dione group content.

Protic solvating agents S which may be used in the process according to the invention are water, alcohols and aliphatic and aromatic carboxylic acids as discussed below. However, the quantity of S to be added in each case to achieve the highest possible content of iminooxadiazinediones is upwardly limited, i.e., as the concentration of quaternary ammonium or phosphonium fluoride in the catalyst mixture is reduced, the selectivity for the preferred formation of iminooxadiazinedione is also reduced. Apart from the successor products arising from the presence of S, substantially only isocyanurates, which have long been known, are obtained.

Suitable monoalcohols include linear and branched, primary, secondary and tertiary alcohols having one to twenty carbon atoms, preferably one to eight carbon atoms. Examples include methanol, ethanol, n- and iso-propanol, 1- and 2-butanol, isobutanol and 2-ethylhexanol.

Suitable organic acids include oxalic acid and weaker acids which have a $pK_a$ of above 2.0, such as formic acid; acetic acid; pivalic acids (optionally substituted by hydroxy groups); malonic, succinic and 1,3-propanedicarboxylic acids (optionally substituted on the $CH_2$ groups); phthalic acid; and salicylic acid. The $pK_a$ value is determined in water at 25° C. (c.f. also Example 5).

The process according to the invention is carried out at a temperature of 20° C. (room temperature) to 200° C., preferably 30° C. to 120° C. and more preferably from 40° C. to 100° C., with partial reaction of the isocyanate groups of the starting isocyanate. The degree of reaction $U_{NCO}$, which is calculated as the quotient of the difference between the NCO content of the starting isocyanate before trimerization and the NCO content of the reaction mixture after termination of the reaction divided by the NCO content of the starting isocyanate before trimerization, is 5% to 50%, preferably 10% to 40%.

Any unreacted monomer may, after deactivation of the catalyst system, be separated off by any known method, for example, by (thin-layer) distillation or extraction, and then recycled.

To deactivate the catalyst system after the desired $U_{NCO}$ has been reached, any of the known prior art methods for terminating the trimerization reaction with isocyanurate formation may be used. Examples include the addition of less than, equal to or greater than stoichiometric amounts of strong acids or acid derivatives with respect to the molar amount of fluoride (MW 19) used (e.g., benzoyl chloride, phosphorous and phosphoric acid and acid esters thereof, but not HF and other weak acids of a $pK_a$ values of above 2.0), adsorptive binding of the catalyst and subsequent removal by filtration and thermal deactivation.

The removal of excess starting (di)isocyanate, provided that it is a low molecular weight "monomeric" (di) isocyanate, is preferably carried out when the products of the process according to the invention are intended for use in the polyurethane lacquer and coating compositions. In this regard the excellent color index and color stability of the products, as well as their high resistance to cleavage to reform the monomeric starting (di)isocyanate, are advantageous.

To prepare the trimers according to the invention, catalyst concentrations (based on the weight of the starting isocyanate and the fluoride ion, MW 19) of 1 ppm to 1%, preferably 1 ppm to 0.1% and more preferably 1 ppm to 0.05%, are sufficient.

According to a continuous embodiment of the process according to the invention, the oligomerization is carried out In a tube reactor. The very low tendency of phosphonium especially the fluoride catalysts to form gel particles in the product, even when used in highly concentrated solution or in pure form, is an advantage in this process. In this continuous process it is possible to use more highly concentrated catalyst solutions than in discontinuous (batch) trimerization reactions. This is because mixing proceeds considerably faster in tubular reactors with turbulent plug flow than it does in stirred tanks, such that the above-mentioned "slow release" mechanism need last for a distinctly shorter period.

The process according to the invention may be carried out either without a solvent or with dilution of the starting isocyanate. Suitable organic compounds include those that are inert towards NCO groups, such as toluene, xylene(s), higher aromatic compounds, esters, ethers, ketones, $C_{12}$–$C_{20}$-alkylsulfonic acid esters and mixtures thereof.

Suitable starting isocyanates for carrying out the process according to the invention include di- or polyisocyanates having a number average molecular weight of 140 to 600 and containing aliphatically, cycloaliphatically and/or araliphatically bound isocyanate groups. The starting isocyanates may be used in pure form or in the form of mixtures. Examples which may be mentioned include hexamethylene diisocyanate (HDI), 2-methylpentane-1,5-diisocyanate (MPDI), 1,3-bis(isocyanato-methyl)-cyclohexane (1,3-$H_6$-XDI), 3(4)-isocyanatomethyl-1-methyl-cyclohexyl isocyanate (IMCI); isophorone diisocyanate (IPDI), bis (isocyanatomethyl)-norbornane (NBDI), 4-isocyanatomethyl-1,8-octane diisocyanate (triisocyanato-nonane, TIN), 1,3-bis(isocyanatomethyl)-benzene, 1,3-bis (2-isocyanatopropyl-2)benzene and bis(4(2)-isocyanatocyclohexyl)methane ($H_{12}$MDI, Desmodur W, available from Bayer AG). The process used for preparing the starting isocyanates, i.e., with or without the use of phosgene, is not important. Preferred starting isocyanates are HDI, MPDI, 1,3-$H_6$XDI, NBDI and mixtures of HDI and IPDI.

In certain instances it is advantageous to use mixtures of starting isocyanates in the process according to the invention, for example, in order to satisfy the property requirements for the product. For example, in the (initial) coating of motor vehicles, polyisocyanate mixtures based on optionally branched, linear-aliphatic diisocyanates such as HDI and cycloaliphatic diisocyanates such as IPDI or $H_{12}$MDI are used. These mixtures are generally prepared by the mixing polyisocyanates that have been separately prepared from the two types of starting diisocyanates. However, it may be advantageous to prepare them by simultaneous mixed trimerization from the corresponding mixture of the monomeric components (EP-A 0,047,452).

Many polyisocyanates based on the known cycloaliphatic diisocyanates are solid. They occasionally have such a high melt viscosity that separation of the monomers by (thin-layer) distillation presents considerable difficulties. For that reason, solvents or flow additives must be used during their processing and sometimes occasionally, also for thin-layer distillation. If too great a loss in the degree of reaction (resin yield) and NCO functionality in the preparation of these polyisocyanates is not acceptable, the resulting isocyanurate polyisocyanates based on cycloaliphatic diisocyanates have solution concentrations of about 70% resin solids and readily processable dynamic viscosities of 1 to 10 Pa·s (23° C.).

To the contrary if mixtures of linear aliphatic isocyanates, such as HDI, and cycloaliphatic diisocyanates, such as IPDI, are trimerized by the process according to the invention with at least partial iminooxadiazine-dione formation, products which are capable of flowing at room temperature (viscosity at 23° C. less than 100 Pa·s) are obtained. These products also exhibit a drastically more rapid fall in viscosity upon the addition of solvents than do prior art products prepared from the same isocyanate starting material and having the same NCO functionality and average molecular weight as shown by Example 6.

Accordingly, the products and product mixtures obtained by the process according to the invention are suitable starting materials for a variety of uses, including the manufacture of optionally foamed plastics as well as lacquers, coating compositions, adhesives and additives.

Before they are used as the isocyanate component in polyurethane systems, the products of the present invention may optionally be modified by reacting the isocyanate groups to incorporate urethane, urea, biuret and/or allophanate groups or by reacting some or all of the NCO groups with reversible blocking agents. Suitable blocking agents include phenols, lactams such as 6-caprolactam, oximes, di- and triazoles, amines such as diisopropylamine and CH-acid compounds such as malonic acid dialkyl esters and acetoacetic ester.

The products prepared according to the invention, optionally in blocked form, are especially suitable for the manufacture of optionally water-dispersible one- and two-component polyurethane coating compositions because their solution and melt viscosities are reduced when compared to isocyanurate-polyisocyanates, while their properties profile is equally high or is improved. Therefore, the HDI-based products of the invention are more stable towards the occurrence of flocculation or turbidity, even when highly diluted in lacquer solvents, when compared to the known corresponding products containing mainly isocyanurate groups. Their resistance towards the effects of moisture (e.g., the formation of a skin in open packaging or the matt appearance of surfaces lacquered at high humidity and a high ambient temperature, so-called "downglossing") is also improved when compared with products containing isocyanurate groups.

The invention is further illustrated but is not intended to be limited by the following examples in which all parts and percentages are by weight unless otherwise specified.

EXAMPLES

Mole percents were determined by NMR spectroscopy and always, unless indicated otherwise, were based on the sum of the NCO secondary products formed as a result of the modification reaction ("trimerization"). Measurements were carried out using a DPX 400 device from Bruker on approximately 5% ($^1$H-NMR) or approximately 50% ($^{13}$C-NMR) samples in dry CDCl$_3$ at a frequency of 400 MHz ($^1$H-NMR) or 100 MHz ($^{13}$C-NMR). As reference for the ppm scale there were chosen small amounts of tetramethylsilane in the solvent with a $^1$H chemical shift of 0 ppm ($^1$H-NMR) or the solvent itself (CDCl$_3$) with a shift of 77.0 ppm ($^{13}$C-NMR). Data for the chemical shift of the compounds in question has been taken from the literature (see Die Angewandte Makromolekulare Chemie 1986, 141, 173–183 and literature cited therein) or obtained by measurement of model substances. 3,5-dimethyl-2-methyl-imino-4,6-diketo-1,3,5-oxadiazine, which was obtained from methyl isocyanate in a yield of approximately 70% following the process described in Ber. d. dtsch. Chem. Ges. 1927, 60, 295, using approximately 3% tri-n-butylphosphine as catalyst, had the following NMR chemical shifts (in ppm): 3.09; 3.08 and 2.84 ($^1$H-NMR, C$\underline{H}_3$) or 148.3; 144.6 and 137.3 ($^{13}$C-NMR, $\underline{C}$=O/$\underline{C}$=N). The products of the process having an iminooxadiazinedione structure have very similar $^{13}$C-NMR chemical shifts of the $\underline{C}$=O/$\underline{C}$=N atoms and can beyond doubt be distinguished as such from other isocyanate secondary products.

Dynamic viscosities were determined at 23° C. using a VT 550 viscosimeter from Haake. By means of measurements at different shear rates it has been ensured that the flow properties of the described polyisocyanate mixtures according to the invention, as well as those of the comparison products, correspond to those of ideal Newtonian fluids. It was therefore unnecessary to indicate the shear rate.

Residual monomer contents were determined by gas chromatography.

The turbidity of the trimer resins was determined using a device from Hach. To that end, scattered light measurements were carried out at 90° to the direction of a light beam having a wavelength of from 400 to 800 nm guided through the resin sample, and were given in units based on formazine standard solutions, TE(F).

The majority of the reactions were carried out using HDI as the isocyanate to be trimerized and catalysts based on tetrabutylphosphonium fluoride under a nitrogen atmosphere. This was merely to demonstrate the advantages of the process according to the invention and was not intended to constitute any limitation of the present invention to the systems or reaction conditions described.

Example 1

Preparation of Quaternary Onium Fluorides (stock solutions)

The solutions were prepared following the procedure proposed in J. Org. Chem. 1989, 54, 4827–4829 for the preparation of ammonium compounds.

a) $Bu_4P^+F^-$ in methanol/isopropanol (stock solution 1a)

953.8 g of a 71.4% $Bu_4P^+Cl^-$ solution in isopropanol (Cyphos 443P, product from Cytec), which corresponds to 2.3 moles of $Bu_4P^+Cl^-$, were dissolved in 1 kg of commercial methanol (approximately 0.2% H2O); 150 g (2.58 moles) of powdered potassium fluoride were added thereto, and stirring was carried out for 24 hours at 20–25° C. (room temperature). The mixture was then filtered and the filtration residue was washed with 2×100 g of commercial methanol; a further 150 g (2.58 moles) of powdered potassium fluoride were added to the combined filtrates, and stirring was carried out for 24 hours at 20–25° C. (room temperature). After subsequent filtration and washing again with 2×100 g of commercial methanol, the mixture was largely freed of excess methanol and isopropanol in a rotary evaporator at a maximum temperature of 30° C. and a pressure of approximately 1 mbar, and filtration was carried out again. The virtually colorless solution obtained had the following properties:

fluoride (with ion-sensitive electrode at pH 5.5): 5.0% chlorine (total, after decomposition, gravimetric): 0.4%

MeOH (gas-chromatographic, after standardization): 16.3% i-PrOH (gas-chromatographic, after standardization): 7.3% b) $Bu_3(C_{14}H_{29})P^+F^-$ in methanol/isopropanol (stock solution 1b)

500 g of a 74.2% $Bu_3(C_{14}H_{29})P^+Cl^-$ solution in isopropanol (Cyphos 3453P, product from Cytec), which corresponded to 0.85 moles of $Bu_3(C_{14}H_{29})P^+Cl^-$, were dissolved in 0.5 kg of commercial methanol (approximately 0.2% $H_2O$); 50 g (0.86 moles) of powdered potassium fluoride were added thereto, and stirring was carried out for 24 hours at 20–25° C. (room temperature). The mixture was then filtered and the filtration residue was washed with 2×50 g of commercial methanol; a further 50 g (0.86 moles) of powdered potassium fluoride was added to the combined filtrates, and stirring was carried out for 24 hours at 20–25° C. (room temperature). After subsequent filtration and washing again with 2×50 g of commercial methanol, the mixture was largely freed of excess methanol and isopropanol in a rotary evaporator at a maximum temperature of 30° C. and a pressure of approximately 1 mbar, and filtration was carried out again. The resulting solution had the following properties:

fluoride (with ion-sensitive electrode at pH 5.5): 3.65% chlorine (total, after decomposition, gravimetric): 0.145%

MeOH (gas-chromatographic, after standardization): 9.1% i-PrOH (gas-chromatographic, after standardization): 3.8% c) $Ph_3(Bu)P^+F^-$ in Methanol (stock solution 1c)

20 g (56.3 mmoles) of $Ph_3(Bu)P^+$ $Cl^-$ (product of Chemconserve) were dissolved in 40 g of commercial methanol (approximately 0.2% $H_2O$). 3.3 g (56.8 mmoles) of powdered potassium fluoride were added thereto, and stirring was carried out for 24 hours at 20–25° C. (room temperature). The mixture was then filtered and the filtration residue was washed with 2×5 g of commercial methanol; a further 3.3 g (56.8 mmoles) of powdered potassium fluoride were added to the combined filtrates, and stirring was carried out for 24 hours at 20–25° C. (room temperature). After subsequent filtration and washing again with 2×5 g of commercial methanol, the mixture was largely freed of excess methanol in a rotary evaporator at a maximum temperature of 30° C. and a pressure of approximately 1 mbar until crystallization began, and filtration was carried out again. During the filtration care was taken to ensure that only potassium salts which formed as a result of further concentration of the solution were separated off and no phosphonium salt remained in the filtration residue (solubility sample). The resulting solution had the following properties:

fluoride (with ion-sensitive electrode at pH 5.5): 3.15% chlorine (total, after decomposition, gravimetric): <0.2%

MeOH (gas-chromatographic, after standardization): 42.8% d) $R_3(Me)N^+F^-$ in methanol/isopropanol (stock solution 1d)

151.3 g of an approx. 90% $R_3(Me)N^+Cl^-$ solution in isopropanol (Adogen 464, product of Aldrich, R represents $C_8$–$C_{10}$ groups with $C_8$ predominating, chlorine content: 7.1%) were dissolved in 170 g of technical grade methanol (approx. 0.2% $H_2O$), combined with 17.6 g of powdered potassium fluoride and stirred for 24 hours at 20–25° C. (room temperature). The mixture was then filtered, the filter residue washed twice with 100 g portions of technical grade methanol and the combined filtrates again combined with 17.6 g of powdered potassium fluoride and stirred for 24 hours at 20–25° C. (room temperature). After subsequent filtration and rewashing twice with 100 g portions of technical grade methanol, excess methanol and isopropanol were largely removed at a maximum of 25° C. and a pressure of approx. 1 mbar in a rotary evaporator to a constant weight, and the mixture was filtered again. The resultant, weakly yellow colored solution had the following properties:

fluoride (with ion-sensitive electrode at pH 5.5): 3.4% chlorine (total, after digestion, gravimetric): 0.2%

MeOH (gas chromatography, after standardization): 13.9% i-PrOH (gas chromatography, after standardization): 2.5%

Example 2

Comparison Examples a) HDI trimerization with an approx. 1.5% tetrabutylphosphonium fluoride solution in 2-ethyl-1,3-hexanediol (approx. 0.1% of $F^-$, preferred catalyst concentration range according to DE-A 38 27 596 or DE-A 3,902,078, which correspond to U.S. Pat. Nos. 4,992,548 and 5,013,838, respectively).

Dissolved gases were initially removed from 200 g (1.19 moles) of HDI in a three-necked flask/stirred apparatus by stirring for approx. 1 hour under a vacuum (0.1 mbar) at 60° C. The vacuum was relieved with nitrogen and the trimerization reaction was then performed until the NCO content of the crude solution was 42.1% over the course of 4 hours by the dropwise addition of the $Bu_4P^+F^-$ stock solution 1a which had been diluted to approx. 0.1% $F^-$ with 2-ethyl-1,3-hexanediol (catalyst requirement: 46 ppm $F^-$, terminated with 103 mg of dibutyl phosphate). Increasing quantities of solid particles were formed during the catalyst addition, which in particular were deposited on the flask walls above the liquid. The resin isolated by filtration of the crude solution through a fluted filter and subsequent film distillation in a short-path laboratory film evaporator at 140° C./0.2 mbar had the properties set forth in Table 1.

When glycol was used as the catalyst solvent instead of the 2-ethyl-1,3-hexanediol, similar results were obtained: excessive turbidity of the crude trimer solutions and resin combined with a constantly falling iminooxadiazinedione formation rate with continued dilution of the catalyst:

b) HDI trimerization with an approx. 1.5% tetrabutylphosphonium fluoride solution in acetonitrile (approx. 0.1% of $F^-$, preferred catalyst concentration range according to DE-A 3,827,596 or DE-A 3,902,078).

c) HDI trimerization with an approx. 1.5% tetrabutylphosphonium fluoride solution in DMF (approx. 0.1% of $F^-$, preferred catalyst concentration range according to DE-A 3,827,596 or DE-A 3,902,078).

Example 2a was repeated using catalysts 2b and 2c. The resultant crude solutions were turbid and contained approx. 3% aprotic solvent and, after a complex filtration operation (gel-like solid particles) and thin film distillation, the resulting products were highly turbid resins (Table 1). The process was very elaborate due to the complex separation of the catalyst solvent and would be difficult to perform commercially.

See also the comments made in Example 4 regarding catalyst addition by other methods ("injection").

TABLE 1

Comparison Examples of catalysis with quaternary phosphonium fluorides (not according to the invention)

| Test no. | Catalyst | Resin turbidity [TE(F)] | Iminooxadiazinedione content in resin trimer mixture [mole %] |
|---|---|---|---|
| 2a | $Bu_4P^+F^-$ | 6.6 | 8 |
| 2b | $Bu_4P^+F^-$ | 4.3 | 22 |
| 2c | $Bu_4P^+F^-$ | 3.1 | 17 |

Example 3

Use of Water as Solvating Agent S

Each of stock solutions 1a, b, c and d were combined with one equivalent of water, based on the fluoride content, and used for HDI trimerization reactions following the procedure described in Example 2a. For subsequent tests 3-2 and 3-3 for each of the stock solutions a–d, the monomer recovered from the preceding test, and sufficient new HDI to make up for the amount that reacted, was trimerized again. No flocculation or formation of solids was observed during the reaction in any of these tests. The isolated resins had a very low level of turbidity and an elevated iminooxadiazinedione content as set forth in Table 2. $U_{NCO}$ was in each case approx. 20%. Any further reaction was terminated by adding the molar quantity of dibutyl phosphate corresponding to the consumption of $F^-$. The $F^-$ requirement of the reaction was between 10 and 30 ppm, based on the weight of starting HDI and the fluoride ion (MW 19).

When the quantity of $H_2O$ in the catalyst was increased to 5 or 10 equivalents per equivalent of $F^-$ in stock solution 1a (tests 3-4 and 3-5), the iminooxadiazinedione content in the trimer mixture was successively reduced. In test 3-5, the more highly viscous HDI secondary products from the NCO/$H_2O$ reaction were also already readily detectable in the resin by NMR spectroscopy. The secondary products were primarily biuret and oxadiazinetrione groups. The latter resulted from the immediate, fluoride-catalyzed incorporation of the carbon dioxide liberated during the NCO/$H_2O$ reaction (c.f. also DE-A 3,902,078).

TABLE 2

Results of the phosphonium or ammonium fluoride-catalyzed HDI trimerization using water as the solvating agent S for the fluoride ion

| Test no. | Catalyst cation | $F:H_2O$ in catalyst approx. (molar) | Resin turbidity [TU(F)] | Iminooxadiazinedione content in trimer mixture [mole %] |
|---|---|---|---|---|
| 3-1a | $Bu_4P^+$ | 1:1 | 0.7 | 39 |
| 3-1b | $Bu_3(C_{14}H_{29})P^+$ | 1:1 | 0.6 | 38 |
| 3-1c | $Ph_3(Bu)P^+$ | 1:1 | 1.2 | 36 |
| 3-1d | $R_3(Me)N^+F^-$ | 1:1 | 1.4 | 36 |
| 3-2a | $Bu_4P^+$ | 1:1 | 0.5 | 42 |
| 3-2b | $Bu_3(C_{14}H_{29})P^+$ | 1:1 | 0.4 | 42 |
| 3-2c | $Ph_3(Bu)P^+$ | 1:1 | 1.2 | 40 |
| 3-2d | $R_3(Me)N^+F^-$ | 1:1 | 1.2 | 39 |
| 3-3a | $Bu_4P^+$ | 1:1 | 0.8 | 43 |
| 3-3b | $Bu_3(C_{14}H_{29})P^+$ | 1:1 | 0.3 | 45 |
| 3-3c | $Ph_3(Bu)P^+$ | 1:1 | 1.3 | 43 |
| 3-3d | $R_3(Me)N^+F^-$ | 1:1 | 0.9 | 40 |
| 3-4 | $Bu_4P^+$ | 1:5 | 0.5 | 35 |
| 3-5 | $Bu_4P^+$ | 1:10 | 1.4 | 32 |

Example 4

Use of Alcohols as Solvating Agent S

All examples relating to the production of products which contained less than 30 mole % of iminooxadiazinedione in the trimer mixture and/or exceeded a turbidity value of 1.5 TE(F) are comparison examples.

Stock solution 1a was used in pure form (test 4-0) or diluted with the alcohols set forth in Table 3 to the concentration set forth in Table 3. The HDI trimerization reactions were carried out following the procedure described in Example 2a. $U_{NCO}$ in each case was approx. 20% and the reactions were terminated by adding the molar quantity of dibutyl phosphate corresponding to the consumption of $F^-$. The $F^-$ requirement for the reaction was 20–50 ppm $F^-$, based on the weight of starting HDI and the fluoride ion (MW 19).

Only when the catalyst was used at very high concentration (test 4-0) were small quantities of solids occasionally observed to be formed in the reaction solution. In this case the crude product was filtered (more easily than in Examples 2b and 2c) before working up by film distillation. It is also possible to inject the catalyst into the HDI to accelerate homogeneous mixing. When the same method was used with the catalyst solutions from Examples 2b and 2c, the nozzles immediately become clogged with solids.

The iminooxadiazinedione content was at the high level according to the invention when the molar quantity of alcohol did not substantially exceed approx. 20 times the fluoride ion concentration, i.e., the catalyst concentration should be no lower than approx. 20 to 30% (c.f. Table 3).

TABLE 3

Results of phosphonium fluoride-catalyzed HDI trimerization using monofunctional alcohols as the solvating agent S for the fluoride ion

| Test no. | Alcohol | $Bu_4P^+F^-$ concentration approx. [%] | F:ROH molar ratio in catalyst | Resin turbidity [TU(F)] | Iminooxadiazinedione content in resin trimer mixture [mole %] |
|---|---|---|---|---|---|
| 4-0 | MeOH/isoPrOH | 73 | 1:2.4 | 0.5* | 45.2 |
| 4-1 | MeOH | 50 | 1:8.7 | 0.67 | 39.8 |
| 4-2 | MeOH | 40 | 1:13 | 0.54 | 40.2 |
| 4-3 | MeOH | 30 | 1:20 | 0.42 | 37.0 |
| 4-4 | MeOH | 5 | 1:165 | 0.39 | 15.8 |
| 4-5 | IsoPrOH | 50 | 1:4.6 | 1.2 | 38.6 |
| 4-6 | IsoPrOH | 5 | 1:88 | 0.94 | 23.0 |
| 4-7 | n-BuOH | 50 | 1:3.8 | 1.3 | 44.2 |
| 4-8 | n-BuOH | 5 | 1:71 | 0.69 | 23.1 |
| 4-9 | IsoBuOH | 50 | 1:3.8 | 0.91 | 45.1 |
| 4-10 | IsoBuOH | 5 | 1:71 | 0.52 | 22.8 |

*in the case of catalyst injection, c.f. text.

Example 5

Use of Organic Acids as Solvating Agent S

Equimolar amounts, based on the weight of the fluoride ion (MW 19), of the organic acids set forth in Table 4 were dissolved in stock solution 1a and the resultant mixtures were used for HDI trimerization reactions following the procedure described in Example 2a. $U_{NCO}$ in each case was approx. 20% and the reactions were terminated by adding the molar quantity of dibutyl phosphate corresponding to the consumption of F$^-$. The F$^-$ requirement for the reaction was 20–50 ppm F$^-$, based on the weight of starting HDI and the fluoride ion (MW 19). No solids formation was observed during the reaction, irrespective of how the catalyst was added. The iminooxadiazinedione contents are set forth in Table 4.

TABLE 4

Results of phosphonium fluoride-catalyzed HDI trimerization using organic acids as the solvating agent S for the fluoride ion

| Formula of S | $pK_a$* (25° C., $H_2O$) | Iminooxadiazinedione content in trimer mixture [mole %] |
|---|---|---|
| HCOOH | 3.38–3.75 | approx. 35 |
| $CH_3COOH$ | 4.75 | approx. 36 |
| $HOCH_2(CH_3)_2CCOOH$ | 4.86-4.87 | approx. 40 |
| $CH_3CH(OH)COOH$ | 4.12 | approx. 38 |
| $(COOH)_2$ | 1.27 | approx. 40 |
| $HOOCCH_2COOH$ | 2.86 | approx. 45 |
| $HOOC(CH_2)_2COOH$ | 4.21 | approx. 50 |
| $HOOC(CH_2)_4COOH$ | 4.41–4.43 | approx. 35 |
| Phthalic acid | 2.58–2.89 | approx. 40 |
| Salicylic acid | 2.97–3.03 | approx. 35 |

*in the case of polybasic acids, the value stated was always pKai; if ranges were stated, there was some variation in values given in the literature (Handbook of Chemistry & Physics, 67$^{th}$ edition, 1986–1987, CRC Press, Boca Raton, Florida, pp. D-163 et seq. or Beilstein online database)

Example 6

HDI/IPDI Co-trimerization

A diisocyanate mixture containing 100 g (0.59 moles) of HDI and 100 g (0.45 moles) of isophorone diisocyanate (IPDI) was introduced into a 250 ml four-necked flask equipped with internal thermometer, stirrer, reflux condenser, gas inlet line and apportioning apparatus for the catalyst solution and dissolved gases were removed at room temperature and a pressure of approx. 0.1 mbar for one hour. The mixture was then heated to an internal temperature of 60° C. while being perfused with a gentle stream of nitrogen. A total of 0.3 g (75 ppm of F$^-$) of stock solution 1a were then added dropwise at this temperature over a period of approx. 20 minutes and trimerization was performed at 60–70° C. until the NCO content of the mixture of 34.0%. The reaction was terminated by adding 0.2 g of di-n-butyl phosphate, stirring was continued for a further hour at 60° C. and then unreacted monomeric diisocyanates were removed by thin film distillation in a short-path evaporator at 0.1 mbar and a temperature of the heating medium of 170° C. The resulting clear (turbidity=1.1 TU(F)) and virtually colorless resin (65.6 g, which corresponded to a yield of 32.8%) had a viscosity in its pure form of 23,000 mPa·s, an NCO content of 20.3% and residual monomer contents of 0.07% HDI and 0.18% IPDI. The iminooxadiazinedione content in the trimer mixture was 41.5%.

Example 7

100 g (0.51 moles) of 1,3-bis(isocyanatomethyl) cyclohexane (Aldrich) were initially pretreated as described in Example 6 and then trimerized for 3 hours at 58–60° C. until the NCO content was 36.6% by adding polyfluoride stock solution 1a in portions; the overall catalyst requirement: 42 ppm F$^-$. The reaction was then terminated by adding 100 mg of di-n-octyl phosphate, stirring was continued for a further hour at 60° C. and unreacted 1,3-bis (isocyanatomethyl)cyclohexane was removed by thin film distillation in a short-path evaporator at 0.2 mbar and a temperature of the heating medium of 140° C. The resulting clear and virtually colorless resin (33.5 g, which corresponded to a yield of 33.5%) had an NCO content of 19.9% and, in its pure form, was still flowable at room temperature (20–25° C.). The viscosity of an 80% solution in n-butyl acetate was 1530 mPa·s and the NCO content was 15.9%. The residual monomer content was 0.07% of 1,3-bis (isocyanatomethyl)cyclohexane and the iminooxadiazinedione content of the trimer mixture was 45.2%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a trimerized polyisocyanate containing at least 30 mole % of iminooxadiazinedione groups (asymmetric trimers) in the trimer mixture which comprises catalytically trimerizing a starting isocyanate selected from organic di- or polyisocyanates having a number average molecular weight of 140 to 600 and containing aliphatically, cycloaliphatically and/or araliphatically bound isocyanate groups in the presence of a quaternary ammonium or phosphonium fluoride trimerization catalyst corresponding to the formula $$R_4E^+F^- \qquad (I),$$

wherein

E represents N or P and

R represents identical or different, optionally branched, aliphatic, aromatic and/or araliphatic $C_1$–$C_{20}$ groups, or two or more R groups form, with one another and with the nitrogen or phosphorus atom, saturated or unsaturated rings, in which the catalyst is i) present in unsolvated form, or ii) blended with a solvating agent S for the fluoride anion, wherein S comprises a member selected from the group consisting of protic compounds having a $pK_a$ value of greater than 2 (determined in $H_2O$ at 25° C.) or oxalic acid, provided that the molar ratio of solvating agent S to fluoride ion, $F^-$, does not exceed 20, and provided that S is not HF or an alcohol having a functionality of 2 or more, or iii) blended with water, wherein the molar ratio of water to fluoride ions ($F^-$) does not exceed 10.

2. The process of claim 1 wherein the starting isocyanate comprises an aliphatic diisocyanate having a molecular weight of 140 to 300 and the trimer mixture contains at least 35 mole% of iminooxadiazinedione groups in the trimer mixture.

3. The process of claim 1 wherein the trimerization catalyst is blended with one or more alcohols having a number average molecular weight of 32 to 250, wherein the concentration of the quaternary ammonium or phosphonium fluoride in the mixture is at least 20wt. %.

4. The process of claim 1 wherein the trimerization catalyst is blended with solvating agent S and the molar ratio of solvating agent S to fluoride ions, $F^-$, does not exceed 10.

* * * * *